United States Patent [19]
Tomiita et al.

[11] Patent Number: 5,476,636
[45] Date of Patent: Dec. 19, 1995

[54] APPARATUS FOR PERFORMING WEATHER RESISTANCE TEST

[75] Inventors: Takashi Tomiita, Abiko; Yoshio Kishima, Osaka; Teruo Iwanaga; Hitoshi Goto, both of Gyoda, all of Japan

[73] Assignees: Building Research Institute, Ministry of Construction, Tsukuba; Dainippon Plastics Co., Ltd., Osaka; Iwasaki Electric Co., Ltd., Tokyo, all of Japan

[21] Appl. No.: 400,531

[22] Filed: Mar. 8, 1995

Related U.S. Application Data

[63] Continuation of Ser. No. 173,929, Dec. 28, 1993, abandoned, which is a continuation of Ser. No. 534,576, Jun. 6, 1990, abandoned.

[30] Foreign Application Priority Data

Jun. 15, 1989 [JP] Japan ................................ 1-150620

[51] Int. Cl.$^6$ .................................................. G01N 17/00
[52] U.S. Cl. .................................. 422/53; 422/67; 436/6; 73/865.6
[58] Field of Search .................................. 436/6; 422/53, 422/67; 73/150 R, 865.6

[56] References Cited

U.S. PATENT DOCUMENTS

| | | | |
|---|---|---|---|
| 2,523,322 | 9/1950 | Ornstein et al. | 374/57 |
| 3,098,720 | 7/1963 | Nettenyer | 422/53 |
| 4,698,507 | 10/1987 | Tator et al. | 250/429 |
| 4,817,447 | 4/1989 | Kashima et al. | 73/865.6 |
| 4,995,273 | 2/1991 | Kisima et al. | 73/865.6 |

FOREIGN PATENT DOCUMENTS 0345003  12/1989  European Pat. Off. .

OTHER PUBLICATIONS

IEEE Transactions on Power Delivery, vol. PWRD–2, No. 3, Jul. 1987.

*Primary Examiner*—Jeffrey R. Snay
*Attorney, Agent, or Firm*—Armstrong, Westerman, Hattori, McLeland & Naughton

[57] ABSTRACT

An apparatus for performing a weather resistance test on a composite material having a metallic, inorganic, or organic base member, and an organic material covering the base member. The apparatus includes a sample holding device disposed in a sample chamber for holding a sample of the composite material. An artificial light source irradiates light substantially in the ultraviolet light area to one surface of the sample. A dipping mechanism dips the sample in a corrosive ionized water, and dew condensation is formed through a temperature control device disposed in the sample holding device, working with a moisture source, for causing dew condensation in the surface of the sample. A cleaning device is provided for cleaning the surface of the sample, and steaming of the sample is performed through the use of a heating element disposed in the sample chamber, and the moistening means, for steaming the sample in an atmosphere of high temperature and high humidity. A control system controls the execution of the operation of the light source, the dipping mechanism, the dew condensation devices, the cleaning device, and the steaming devices, in a sequential manner.

2 Claims, 13 Drawing Sheets

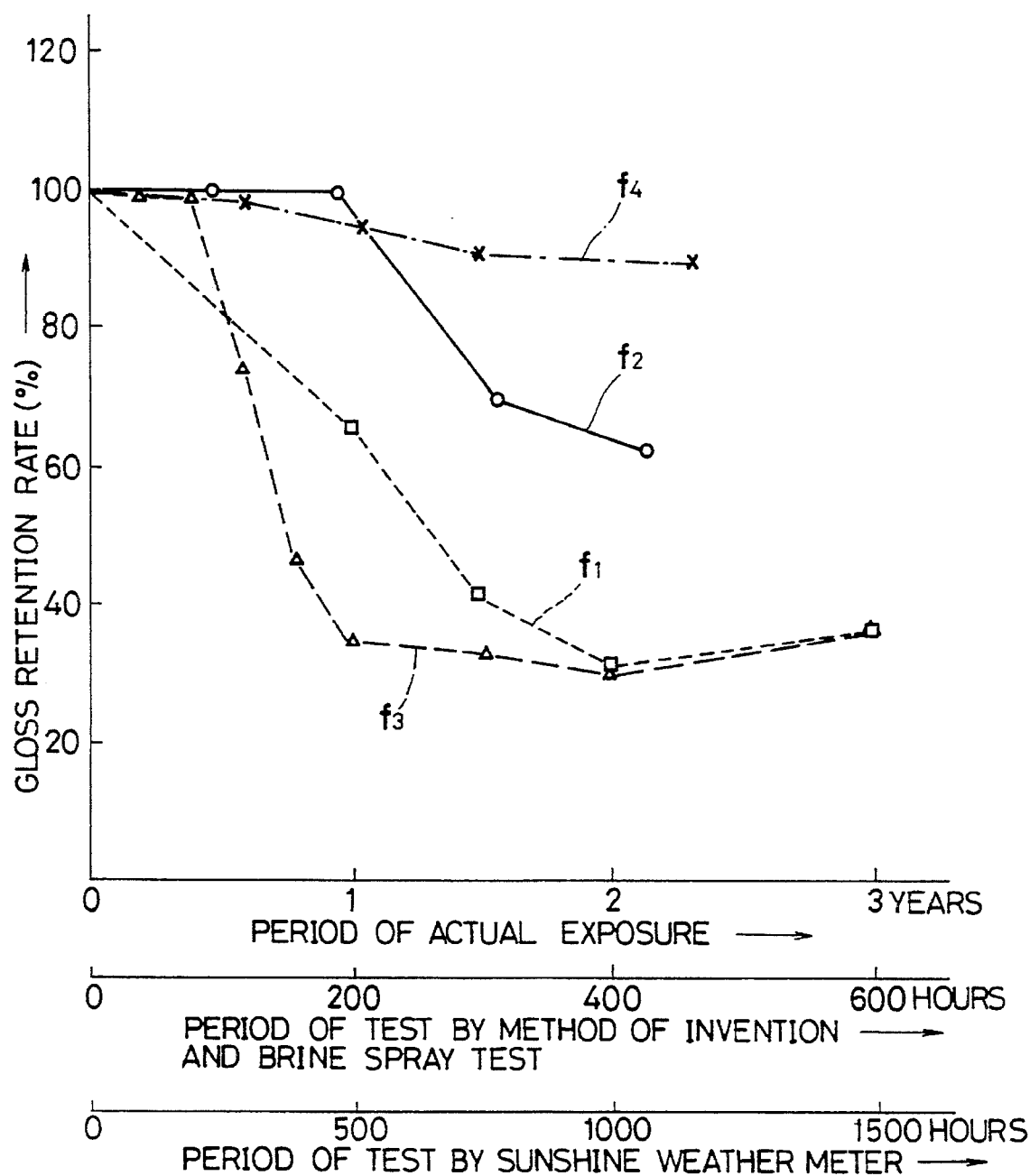

APPARATUS FOR PERFORMING WEATHER RESISTANCE TEST

This application is a continuation of application Ser. No. 08/173,929 filed Dec. 28, 1993, now abandoned, which was a continuation of application Ser. No. 07/534,576 filed Jun. 6, 1990, now abandoned.

BACKGROUND OF THE INVENTION

The present invention relates to a method of and an apparatus for performing a weather resistance test. More particularly, the invention is concerned with a method of and apparatus for performing a weather resistance test capable of producing, in a short time, test results having close correlation to actual degradation which is caused on a composite material having a base member of a metal, an inorganic material or an organic material and a coating layer of an organic material, e.g., a plastic when such a composite material is left in natural environment including corrosive substances.

In general, weather resistance of plastics and materials coated with plastics is tested by a weather resistance testing apparatus as specified by JIS (Japanese Industrial Standards) B 7751–7754. Usually, this testing apparatus employs a light source such as a carbon arc lamp or a xenon lamp for generating light rays which are applied to the test samples to promote the degradation thereby enabling the test to be finished in a short time.

In general, structures in seashore areas are exposed to air which is rich in salt, while offshore structures are held in corrosive condition due to contact with sea water. Thus, structures on seashores and offshore structures are exposed to much severe condition as compared with structures in environment which do not contain salty air. Furthermore, in industrial areas where there are many factories, structures are under severe conditions as they are often subjected to acidic rain. The ordinary weather test apparatus mentioned above, therefore, cannot perform promoted test results with good correlation to actual degradation, when the material to be tested is a composite material composed of a metallic substrate and a coating plastic, as in the cases of materials used in structures on seashore areas, offshore structures, ships and fishery equipments, as well as structures in industrial areas.

A composite weather resistance testing apparatus has been known in which a brine spray process is combined with functions of ordinary weather meter such as light irradiation and dew condensation to enable evaluation of resistance to salty environment. A marine exposure promotion testing apparatus is also known in which, as disclosed in Japanese Utility Model Laid-Open No. 55-105153, the tested material is subjected to light irradiation, brine spray and strain.

The known composite testing apparatus and marine exposure promotion testing apparatus, however, can provide only a small ultraviolet irradiation intensity, e.g., 6 mW/cm$^2$, due to the use of a carbon arc amp or a xenon lamp as the light source. In addition, the speed of degradation of the tested material is too low and the test results do not show close correlation to actual degradation, due to the fact that the test operation includes only the testing processes such as light irradiation, brine spray, dew condensation and generation of strain.

SUMMARY OF THE INVENTION

In order to overcome the above-described problems encountered with known weather resistance testing method and apparatus incorporating brine condition, the present invention is aimed at providing a method of and an apparatus for performing a weather resistance test which can provide, in a short time, test results of good correlation to the actual natural degradation under corrosive environment rich in salt or acidic rain.

To this end, according to one aspect of the present invention, there is provided a method of performing a weather resistance test on a composite material having a base member made of a metallic, inorganic or an organic material and a covering material of an organic material covering the base member, the method having the steps of preparing a sample of the composite material, irradiating step for irradiating the sample with light rays including ultraviolet rays from an artificial light source, dipping step for dipping the sample in a corrosive ionized water, and dew condensation step for causing dew condensation on the surface of the sample, the method being characterized by comprising: a cleaning step for cleaning the surface of the sample; and a steaming step for subjecting the sample to an atmosphere having high temperature and high humidity.

The cleaning step removes, from the surface of the test piece, matters which have been formed in the step of irradiation with lights including ultraviolet rays, so as to facilitate execution of a subsequent step, e.g., to facilitate permeation of ionized water such as brine in the dipping step executed subsequently to the light irradiation step, thereby promoting the degradation. The steaming step for exposing the test piece to an atmosphere of high temperature and high humidity simulates a hot and humid weather condition, thus contributing to prompt development of results with close correlation to actual degradation.

According to another aspect of the present invention, there is provided an apparatus for performing a weather resistance test on a composite material having a metallic, inorganic or an organic base member and an organic material covering the base member, comprising: sample holding means for holding a sample of the composite material; irradiating means including an artificial light source for irradiating one surface of the sample with light rays containing ultraviolet rays; dipping means for dipping the sample in a corrosive ionized water; dew condensation means including moistening means for causing dew condensation in the surface of the sample; cleaning means for cleaning the surface of the sample; steaming means including heating means and humidifying means for steaming the sample in an atmosphere of high temperature and high humidity; and control means for controlling execution of operations of the irradiating means, dipping means, dew condensation means, cleaning means and steaming means in a sequential manner.

The use of the cleaning means for cleaning the test piece surface and the steaming means for exposing the test piece to an atmosphere of high temperature and high humidity makes it possible to provide a weather resistance testing apparatus which is capable of promptly developing test results with high degree of correlation to the actual degradation.

These and other objects, features and advantages of the present invention will become clear from the following description of the preferred embodiments when the same is read in conjunction with the accompanying drawings.

BRIEF DESCRIPTION OF THE DRAWINGS

FIGS. 8 to 13 are graphs showing changes in a gloss retention rate test samples as observed when the samples were tested by the method of the present invention and conventional methods 1 and 2, as well as by an actual exposure.

DESCRIPTION OF THE PREFERRED EMBODIMENTS

Preferred embodiments of the present invention will be described hereinunder.

Figure 1:
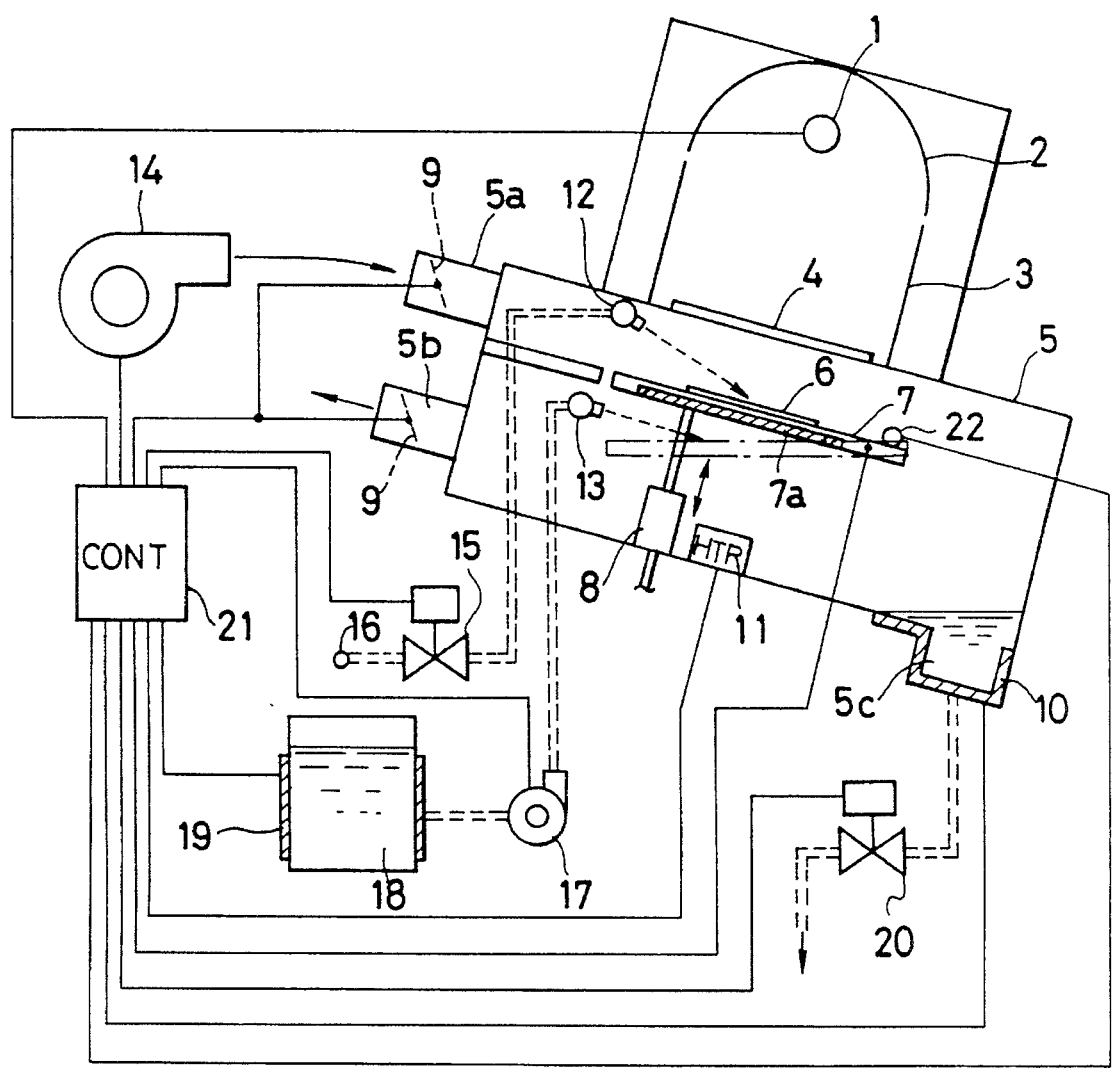
FIG. 1 is a schematic diagrammatic illustration of an embodiment of the weather resistance testing apparatus in accordance with the present invention.

Referring to FIG. 1 which is a schematic diagrammatic illustration of an embodiment of the weather resistance testing apparatus in accordance with the present invention, the apparatus has a light source 1 which includes a metal halide lamp capable of radiating considerably great energy in a predetermined wavelength region, e.g., 250 to 550 nm, a filter for substantially restricting the wavelength region to 300 to 450 nm, and a water-cooling jacket. The light source 1 is disposed in a reflector which is composed of a dome-shaped collimating main reflector plate 2 and collimating auxiliary reflector plates 3. Numeral 4 denotes a shield plate made of quartz and capable of transmitting ultraviolet rays while hermetically isolating the light source from a sample chamber 5 disposed beneath the light source unit.

The sample chamber 5 is inclined at, for example, 15° due to a specific arrangement of a later-mentioned sample holder. The light source unit, which is mounted on the sample chamber 5. is inclined correspondingly. The sample holder 7 in the form of a tray and capable of holding a sample 6 thereon is disposed in the sample chamber 5 for a pivotal movement about an axis near one end thereof. More specifically, the sample holder 7 is adapted to be moved by an actuator 8 so as to pivot between an inclined position where it is held at about 15° inclination with respect to horizontal plane to enable a later-mentioned cleaning agent from a later-mentioned spray nozzle to smoothly flow down without stagnation and a horizontal position where it enables the test sample 6 held thereon to be dipped in an ionized water. Temperature control means 7a such as water-cooling means or electronic cooling means are associated with the sample holder 7.

An air inlet port 5a and an air outlet port 5b are provided in one of the side walls of the sample chamber 5 so as to project therefrom, and dampers 9,9 for selectively opening and closing these ports are provided in these ports 5a and 5b. A dampening water reservoir 5c is provided at a bottom corner of the sample chamber 5. A moistening heater 10 is provided so as to surround the water reservoir 5c and a heater 11 for heating the interior of the sample chamber 5 is provided on the bottom of the sample chamber 5. The aforementioned spray nozzle 12 for spraying a cleaning agent towards the sample holder 7 is disposed in the sample chamber 5 at a position above the sample holder 7 in the inclined state. A nozzle 13 for supplying ionized water is disposed at a position which is on an obliquely upper side of the sample holder 7 held in horizontal posture. The cleaning agent may be a water, a surface active agent, a water containing air, alcohol or the like. The ionized water may be an aqueous solution of NaCl, $MgCl_2$, $H_2SO_4$ and NaOH, a mixture of such aqueous solutions and natural sea water.

A temperature controlling blower 14 is capable of supplying air into the sample chamber 5 through the air inlet port 5a so as to maintain a predetermined temperature of the sample 6 on the sample holder 7. The cleaning agent spray nozzle 12 is connected through a pipe having a solenoid valve 15 to a cleaning agent supply port 16, while the ionized water nozzle 13 is connected to the ionized water tank 18 via an ionized water pump 17. The ionized water tank 18 is provided with a heater 19 for maintaining the temperature of the ionized water at a predetermined level. The water reservoir 5c provided at the bottom corner of the sample chamber 5 is connected to a draining port through a draining solenoid valve 20. The light source 1, temperature control blower 14, automatic damper 9, cleaning agent solenoid valve 15, ionized water pump 17, draining solenoid valve 20 and heaters 10, 11 and 19 are controlled by a controller 21.

A description will be given of an example of the weather resistance testing method of the invention which is carried out by using the weather resistance testing apparatus having the described construction. The sample 6 held on the sample holder 7 is subjected to ultraviolet irradiation of an intensity of 50 to 80 $mW/cm^2$ caused by the activation of the light source 1 for a predetermined period, e.g., 6 to 18 hours, while being held in an atmosphere of a relative humidity of 20 to 80%, e.g., 30%, and while being maintained at a constant temperature, e.g., 40° C.±1.0° C. to 100° C.±1.0° C., by the air which blown by the blower 14. Then, the light source 1 is turned off to terminate the ultraviolet irradiation and the solenoid valve 15 is operated to supply an ion-exchange water of 20° to 80° C., e.g., 60° C. so that the ion exchange water is sprayed from the spray nozzle 12 for 30 seconds, thereby removing matters depositing on the surface of the sample. This cleaning step facilitates permeation of an ionized water such as brine into the sample in the subsequent step.

Then, the actuator 8 is operated to set the sample holder 7 horizontally and the ionized water pump 17 starts to operate so that an ionized water in the ionized water tank 18, e.g., a 5% NaCl aqueous solution (pH 6.5 to 7.5) of 40° C., is supplied to the tray-type sample holder 7 from the spray nozzle 13, whereby the sample 6 is dipped in the ionized water for 10 seconds. Subsequently, the actuator 8 operates again to incline the sample holder 7 so as to allow the ionized water to flow down from the sample holder 7 and then the draining solenoid valve 20 operates to discharge the water. Then, the blower 14 operates again to supply dried air so as to dry the sample at a drying rate of 1° to 5° C./min for 30 minutes. The humidifying heater 10 is then controlled to maintain a relative humidity of 95% within the sample chamber. Meanwhile, ion exchange water for cleaning purpose is supplied to the portion around the humidifying heater in the sample chamber. In addition, temperature control means 7a operates in accordance with a signal from a temperature sensor 22 on the sample holder 7, so as to lower the temperature of the sample holder 7 down to a predetermined temperature below the dew point, e.g., down below about 30° C., so that dew condensation takes place on the surface of the sample 6 held by the sample holder 7, whereby a heat shock is applied to the sample 6.

The sample 6 is held under this dewing condition for a predetermined time, e.g., 1 hour, and, thereafter, the sample holder 7 is set to a horizontal position. The ionized water pump 17 is then operated to supply ionized water again from the ionized water nozzle 13 so as to dip the sample 6 in the ion water for 10 seconds. The sample holder 7 is then inclined again. The application of heat shock and the subsequent dipping in the ion water greatly promote the corrosion.

Then, after the sample 6 is dried, the humidifying heater 10 and the sample chamber heater 11 are controlled to create a highly humid and hot condition, e.g., 95% relative humidity and 50° C., in the sample chamber 5, and the sample 6 is exposed to this humid and hot atmosphere for 12 hours. The sample 6 is heated and moistened as a result of execution of this steaming step. The ultraviolet irradiation is then conducted again following the execution of the steaming step. In this step, ultraviolet rays of high intensity is applied to the surface of the sample which is in a steamed state, so that a very severe condition is realized to further promote the degradation. These steps are then executed repeatedly and cyclically.

The described method of executing weather resistance test imparts to the samples conditions which closely approximate natural conditions in the seashore areas or offshore areas and can provide, in a short time, weather resistance test results with close correlation to the natural degradation, by virtue of addition of the cleaning and steaming steps.

In the described embodiment, the steaming step for exposing the sample to an atmosphere of high temperature and high humidity is executed between the ionized-water dipping step and ultraviolet irradiation step. This, however, is not exclusive and similar effects are obtainable also when the steaming step is executed, for example, after the cleaning step or before or after the forcible dew condensation step.

In the described embodiment, only one spray nozzle for spraying the cleaning agent is provided above the sample. The number and positions of the spray nozzle or nozzles, however, may be freely determined in accordance with factors such as the shape and size of the sample holder. The ionized water dipping step in the described method is executed by dipping the sample in the ionized water filling the tray-type sample holder. This, however, is only illustrative and the dipping may be effected by spraying the ionized water onto the sample held on the sample holder in the inclined state as in the case of cleaning, or by immersing for a predetermined time the sample holder together with the sample in a bath of the ionized water contained in a separate ionized water tank and then lifting the sample holder. By using an acidic solution such as of $H_2SO_4$ as the ionized water, it is possible to evaluate the resistance to acidic rain.

Tests were conducted in accordance with the weather resistance testing method of the invention and also by conventional weather resistance testing methods and actual exposure, in order to confirm the effects brought about by the invention, the results being shown below.

(1) Conditions of Testing Method According to Invention

Light source: metal halide lamp 4 KW

Irradiation light wavelength: 300 to 450 nm

Black panel temperature (when irradiated with ultraviolet rays): 63° C.±3° C.

Ultraviolet rays intensity on sample surface: 80±5 mW/cm$^2$

Ultraviolet irradiation time: 6 hours

Cleaning period: 30 seconds (after completion of ultraviolet ray irradiation)

Cleaning agent: Ion exchange water

Cleaning agent temperature: 60° C.

Rate of spray of cleaning agent: 9 cc per 1 cm$^2$ of sample surface

Pressure of spray of cleaning agent: 1.5 kg/cm$^2$

Ionized water: 5% Nacl solution

Ionized-water dipping period: 10 seconds

Ionized water temperature: 40° C.

Drying period: 30 minutes

Drying rate: 1° to 5° C./min

Sample chamber air humidity at dewing: 95% RH

Sample temperature at dewing: 30° C.

Dewing period: 6 hours

Sample chamber air temperature at steaming: 50° C.

Sample chamber air humidity at steaming: 95% RH

Steaming period: 11.5 hours (2) Conditions of Actual Exposure Test

Period: 3 years (as from Mar. 26, 1985)

Place: A facility for general research of marine technology, Ministry of Construction (Suruga Bay, Japan)

(3) Conditions of Conventional Testing Method 1 (With Sunshine weather meter)

Light source: Sunshine carbon arc lamp

Irradiation light wavelength: 280 to 1400 nm

Black panel temperature: 63° C.±3° C.

Ultraviolet rays intensity on sample surface: 5 mW/cm$^2$

Water spray: 18 minutes within 2 hours (4) Conditions of Conventional Testing Method 2 (brine spray test according to JIS-Z 2371)

Nacl solution: 5±1%

Test room temperature: 35°±1° C.

Brine tank temperature: 35°±1° C.

Continuous spray

The following six types of coated plates (a) to (f) were used as the test samples:

(a) Vinyl chloride laminate galvanized steel sheet (laminate layer thickness: 200 μm)

(b) Galvanized steel sheet coated with vinyl chloride sol (coating layer thickness: 300 μm)

(c) 55% Al—Zn-plated steel sheet coated with vinyl chloride sol (coating layer thickness: 200 μm)

(d) Galvanized steel sheet coated with fluororesin (coating layer thickness: 30 μm)

(e) Fluororesin laminate galvanized steel sheet (laminate layer thickness: 38 μm)

(f) Galvanized steel sheet coated with polyester (coating layer thickness: 18 μm)

These samples were tested by the testing methods shown above, and the color difference ΔE* in terms of a CIE1976L*, a*, b* space colorimetric system and gloss retention rate were measured on these tested samples, the results being shown in FIGS. 2 to 13. The color difference ΔE* is the measured value of a change in hue of one side of each sample, while the gloss retention rate was obtained in accordance with the following formula, on the basis of the change in the 60° mirror surface reflectivity as measured by a gloss meter on each sample:

Gloss retention rate={(gloss after test)/(initial gloss)}×100 (%)

The same tests were also executed on the same samples with scratches formed on these samples so as to reach the underlying metallic layers, for the purpose of evaluation of corrosion and change in the coating layers on these samples, the results being shown in Tables 1 and 2. In case of the actual exposure test, however, no scratch was formed and results of observation of cut sections are shown in these tables.

Figure 2:
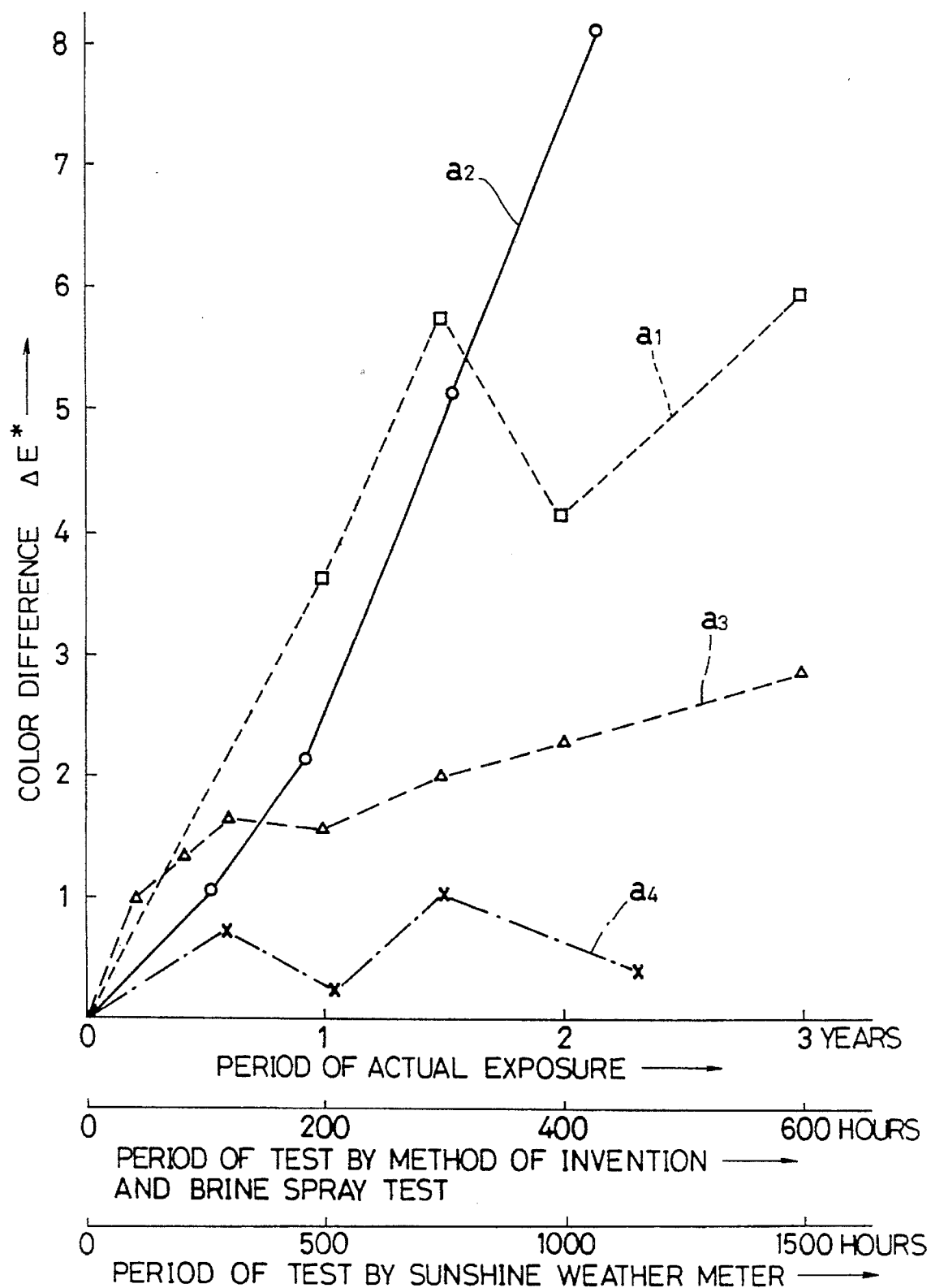
FIGS. 2 to 7 are graphs showing changes in a color difference value ΔE* of test samples as observed when the samples were tested by the method of the present invention and conventional methods 1 and 2, as well as by an actual exposure.

The curves $a_1$, $a_2$, $a_3$ and $a_4$ shown in FIG. 2 represent the changes in the color difference $\Delta E^*$ on the vinyl chloride laminate galvanized steel sheet tested by the actual exposure, testing method of the invention and conventional testing methods 1 and 2, respectively. In case of the actual exposure test, the $\Delta E^*$ value showed a rapid rise up to 5 or higher in 18 months after the commencement of the test, and is then substantially saturated as will be seen from the curve $a_1$. The weather resistance testing method of the present invention showed a tendency substantially the same as that in the actual exposure test as shown by the curve $a_2$. It was confirmed that the $\Delta E^*$ value equivalent to that obtained in 18 months in the actual exposure can be attained in quite a short time of 300 hours when the testing method of the invention is used.

On the other hand, in the case of the conventional testing method 2, no substantial change was observed in the $\Delta E^*$ value. In the conventional testing method 1 also, the change in the $\Delta E^*$ value obtained in 1500 hours after the commencement of the test was as small as that obtained in 200 hours in the testing method of the invention.

Figure 3:
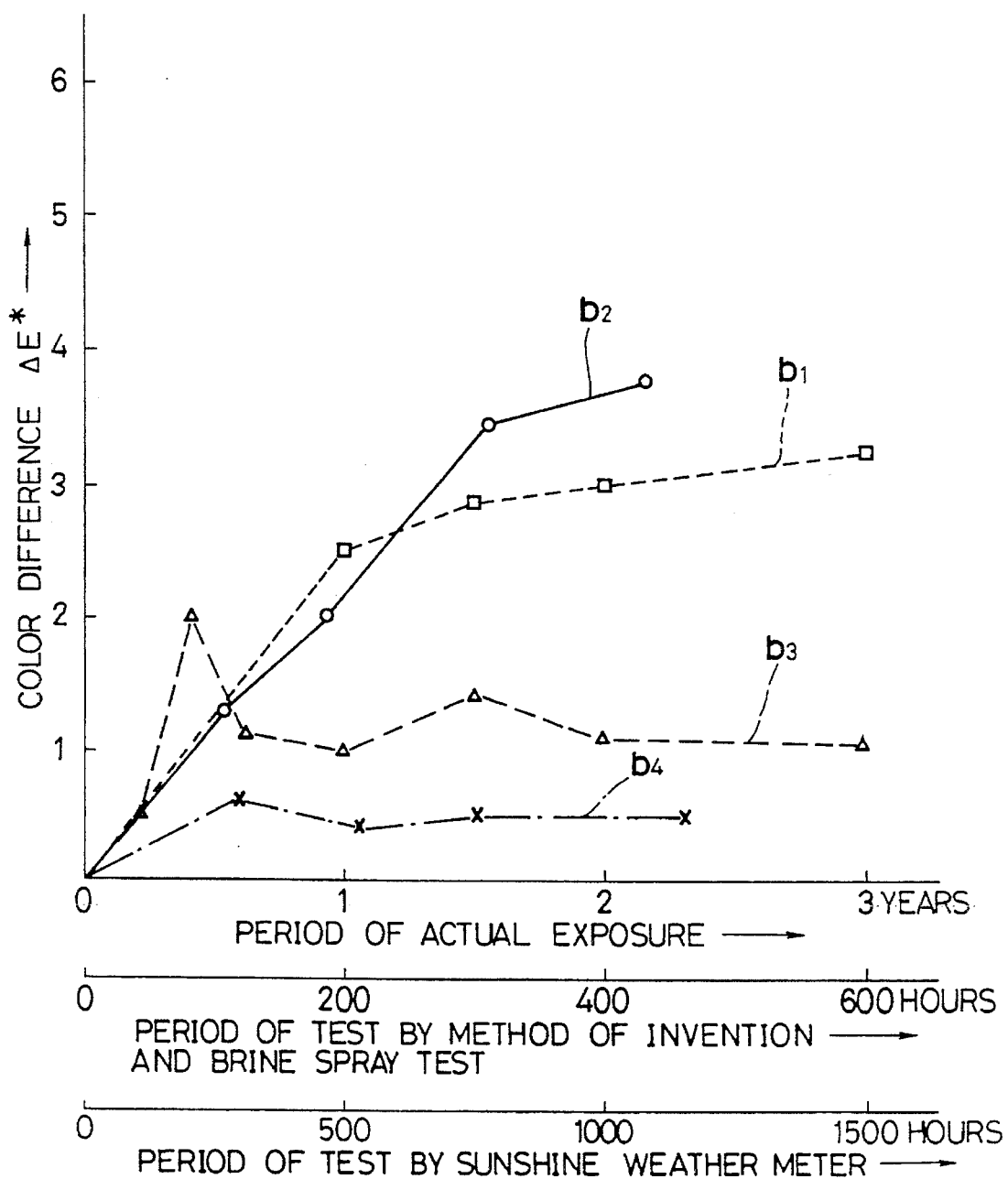
Figure 4:
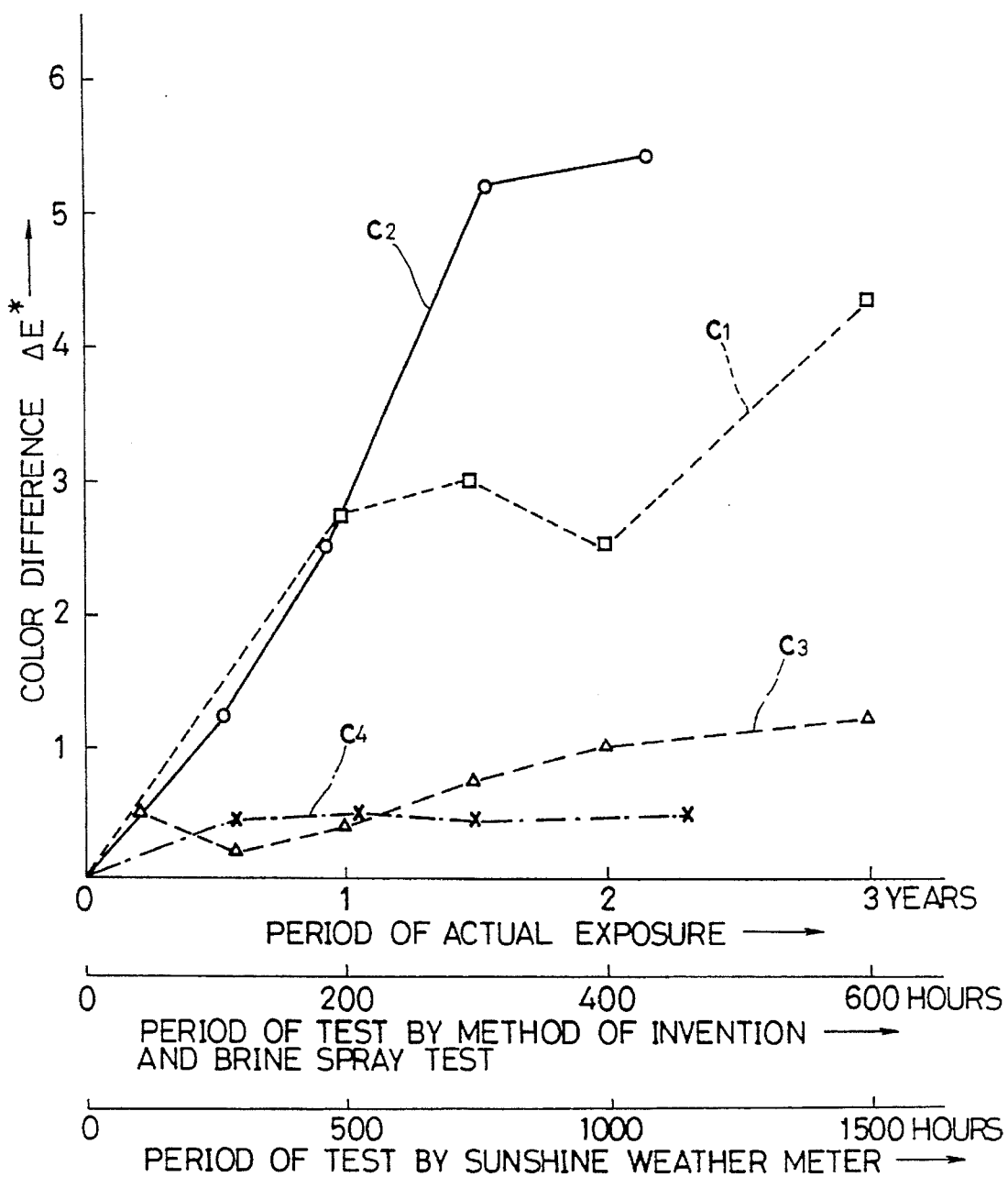

The curves $b_1$, $b_2$, $b_3$ and $b_4$ shown in FIG. 3 and the curves $c_1$, $c_2$, $c_3$ and $c_4$ shown in FIG. 4 represent the changes in the color difference $\Delta E^*$ on the samples of the galvanized steel sheet coated with vinyl chloride sol and Al—Zn-plated steel sheet coated with vinyl chloride sol, respectively, tested by the actual exposure, testing method of the invention and conventional testing methods 1 and 2, respectively. In case of the actual exposure test, the $\Delta E^*$ value showed a rapid rise in 12 months after the commencement of the test, and is then substantially saturated in both types of samples, as will be seen from the curves $b_1$ and $c_1$. The weather resistance testing method of the present invention showed a tendencies substantially the same as that in the actual exposure test as shown by the curves $b_2$ and $c_2$. Namely, the $\Delta E^*$ value rapidly increased in 300 hours after the commencement of the test and then saturated. Furthermore, the $\Delta E^*$ values attained in 200 hours of the test by the testing method of the invention well coincided with those obtained in 12 months in the actual exposure test, thus proving specifically high degree of closeness of correlation therebetween. It will also be understood that the conventional testing methods 1 and 2 could not provide changes in the $\Delta E^*$ values equivalent to those of the actual exposure test and the testing method of the invention, despite prolonged testing periods.

Figure 5:
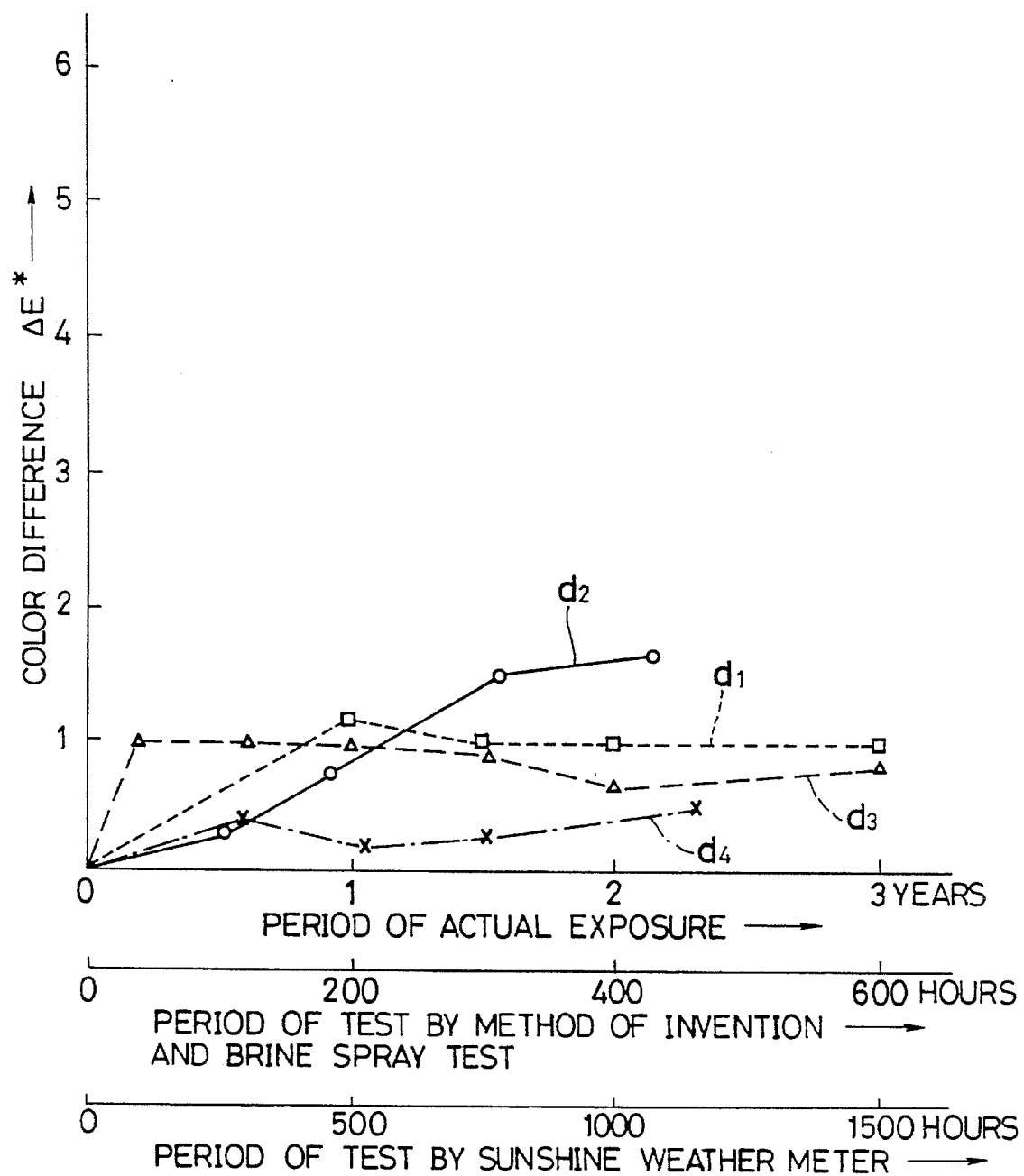
Figure 6:
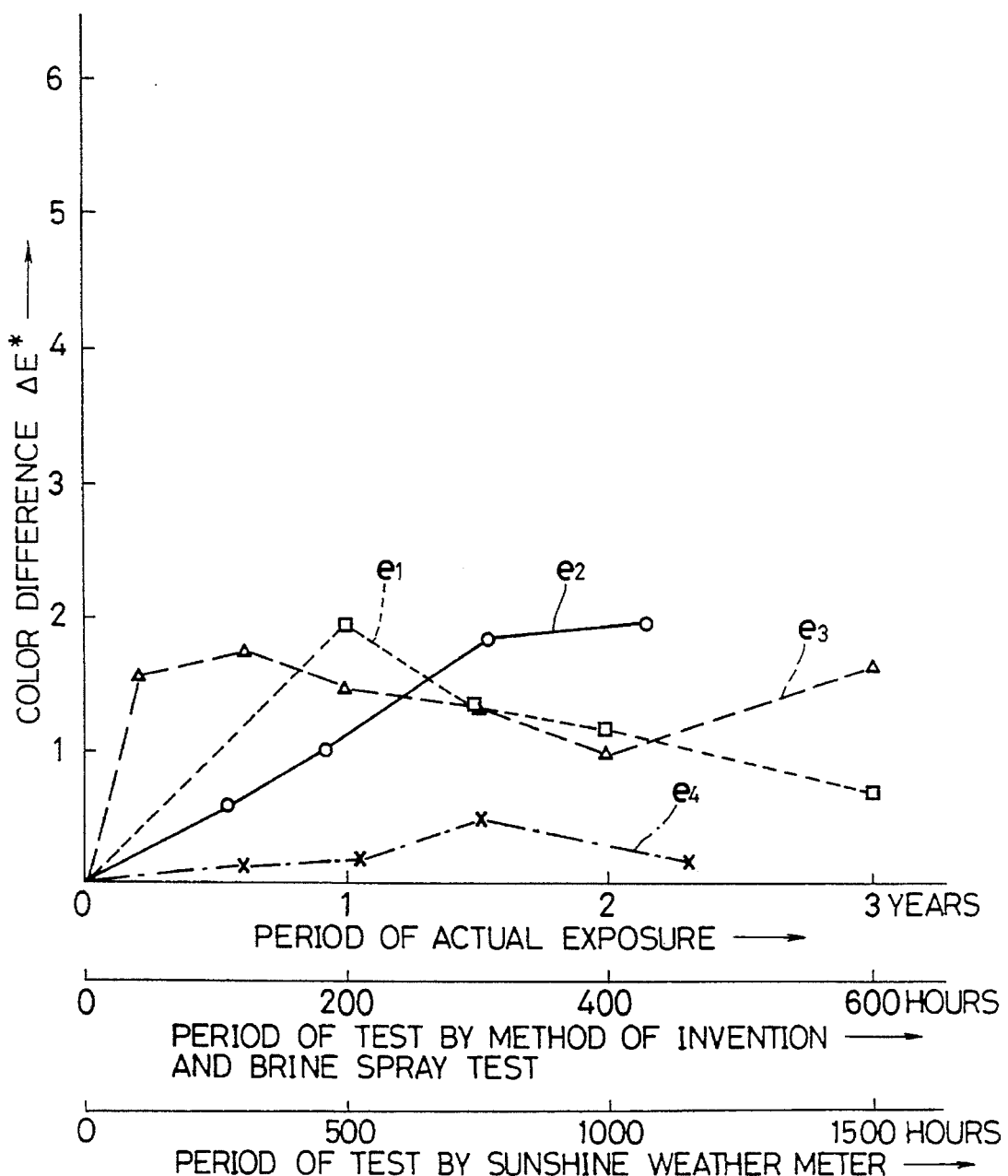
Figure 7:
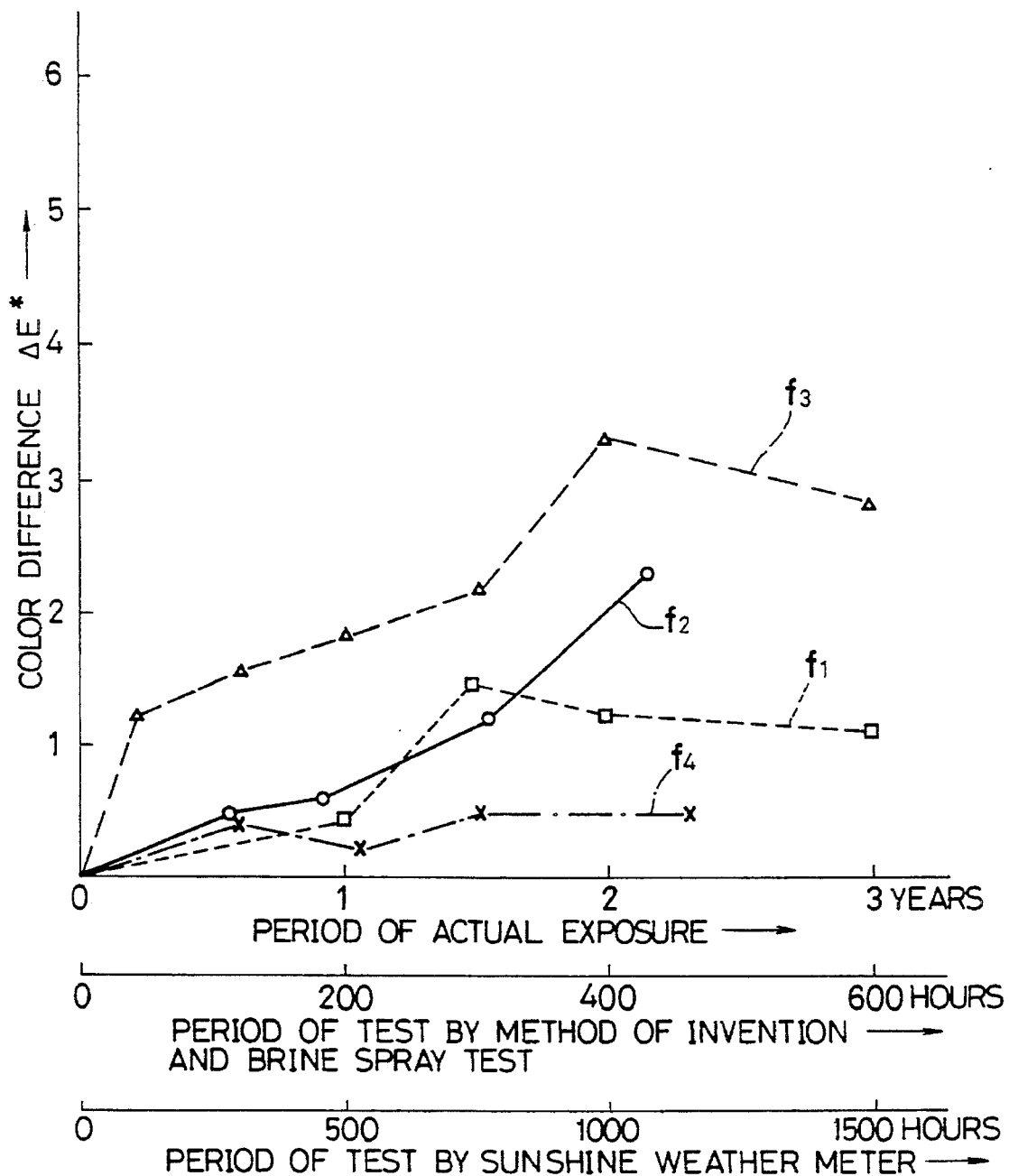

The curves $d_1$, $d_2$, $d_3$ and $d_4$ shown in FIG. 5, curves $e_1$, $e_2$, $e_3$ and $e_4$ shown in FIG. 6, and the curves $f_1$, $f_2$, $f_3$ and $f_4$ shown in FIG. 7 represent the changes in the color difference $\Delta E^*$ on the samples of the galvanized steel sheet coated with fluororesin, the fluororesin laminate galvanized steel sheet and galvanized steel sheet coated with polyester, respectively, as tested by the actual exposure, testing method of the invention and conventional testing methods 1 and 2, respectively. These samples showed smaller values of change in the color difference $\Delta E^*$ than the samples employed in the preceding tests. Nevertheless, the testing method of the invention provided results with close correlation to the results of the actual exposure test.

Figure 8:
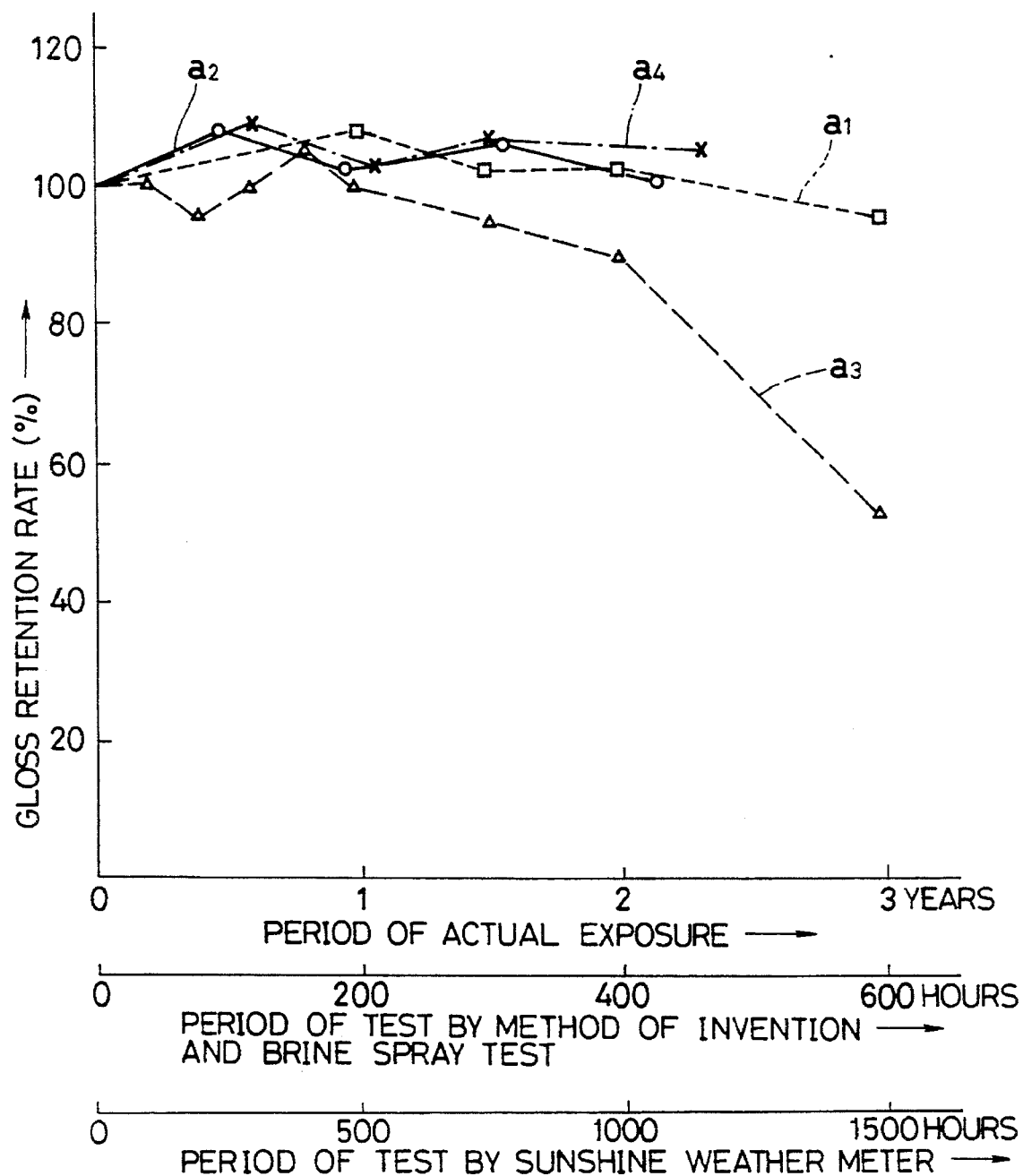

In FIG. 8, the curves $a_1$, $a_2$, $a_3$ and $a_4$ show the results of measurement of changes in the gloss retention rate as obtained when samples of vinyl chloride laminate galvanized steel sheet were tested by the actual exposure, testing method of the invention, and the conventional testing methods 1 and 2. As will be seen from the curves $a_1$ and $a_2$, the samples tested by the actual exposure and the testing method of the invention showed substantially constant values of gloss retention rate, thus proving a high degree of closeness of correlation therebetween. On the other hand, the sample tested by the conventional testing method 1 showed a significant reduction in the gloss retention rate in relation to time, unlike the result of the actual exposure test, as will be seen from the curve $a_3$.

Figure 9:
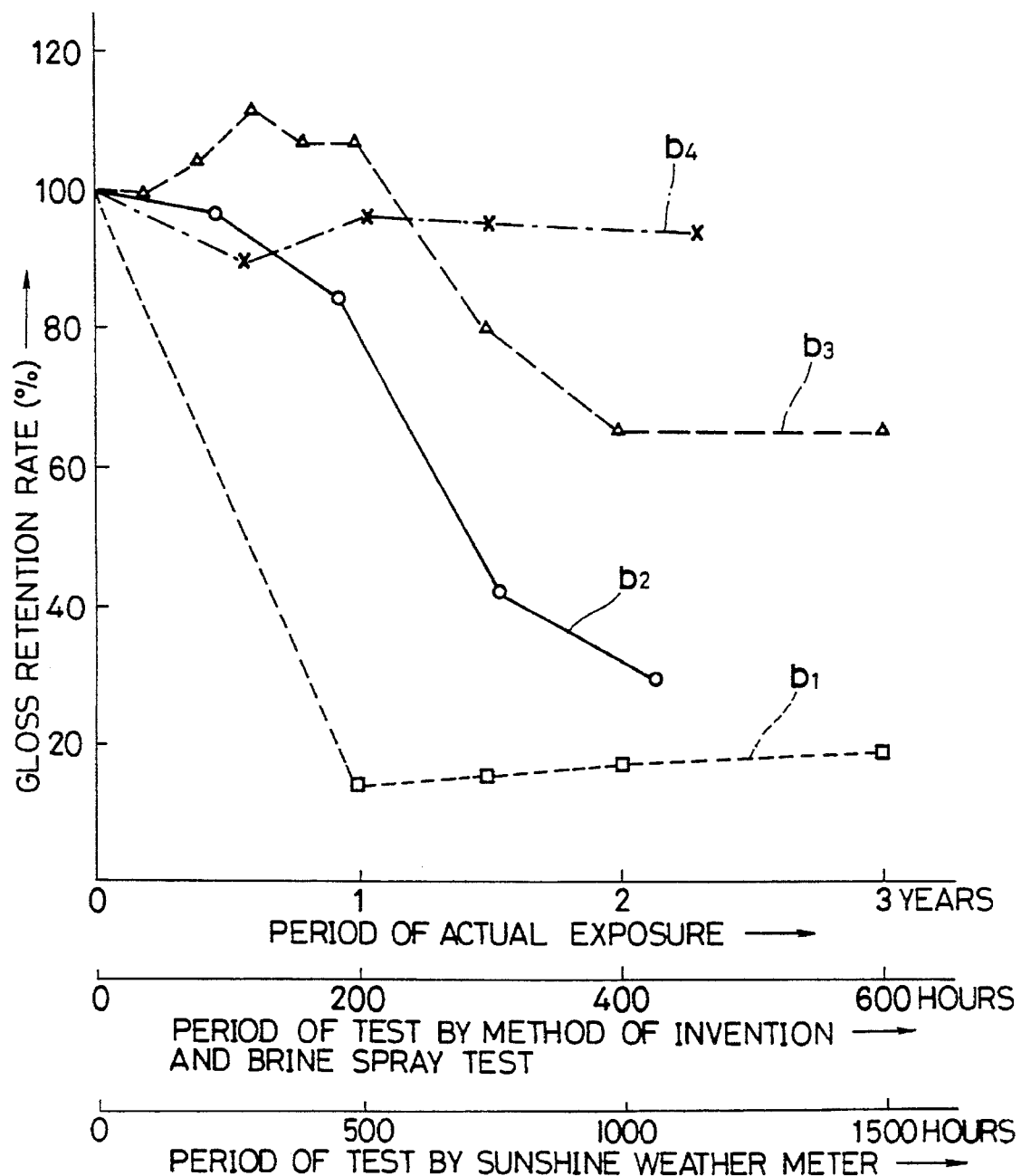

In FIG. 9, the curves $b_1$, $b_2$, $b_3$ and $b_4$ show the results of measurement of changes in the gloss retention rate as obtained when samples of galvanized steel sheet coated with vinyl chloride sol were tested by the actual exposure, testing method of the invention, and the conventional testing methods 1 and 2. The sample tested by the actual exposure showed a rapid decrease in the gloss retention rate in 12 months after the commencement of the test and, thereafter, a substantially constant value of the gloss retention rate, as will be seen from the curve $b_1$. On the other hand, the sample tested by the testing method of the invention initially showed a gentle reduction in the gloss retention rate but the rate started to rapidly decrease about 200 hours after the start of the test and reached, in 400 hours after the start of the test, the value which is substantially the same as that reached in 24 months in the actual exposure test. In contrast, the test according to the conventional testing method 2 showed no significant change in the gloss retention rate, while the conventional method 1 caused an occasional rise in the gloss retention rate followed by a reduction. The change observed in the conventional method 1, however, much less significant than the result of the test according to the testing method of the present invention.

Figure 10:
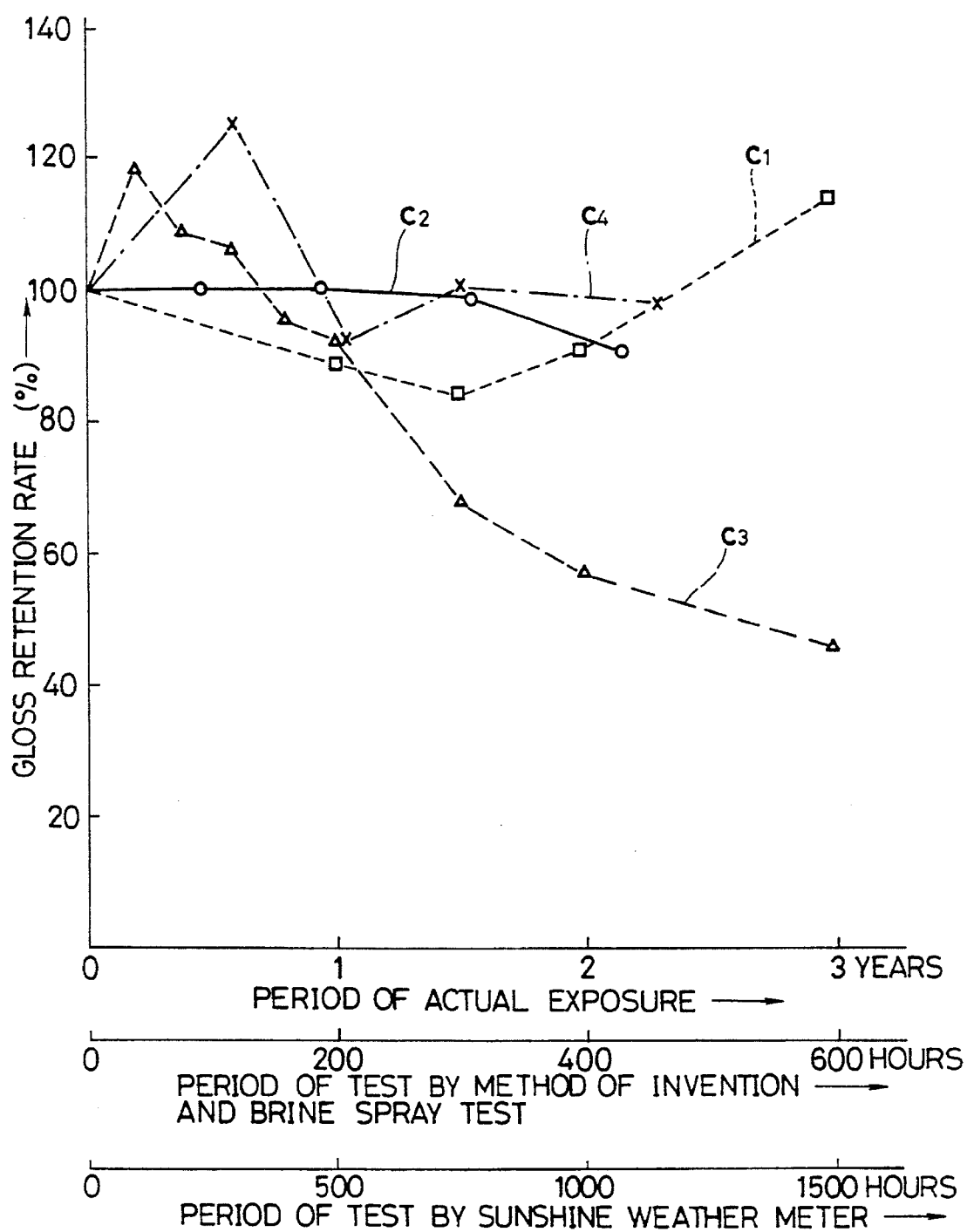
Figure 11:
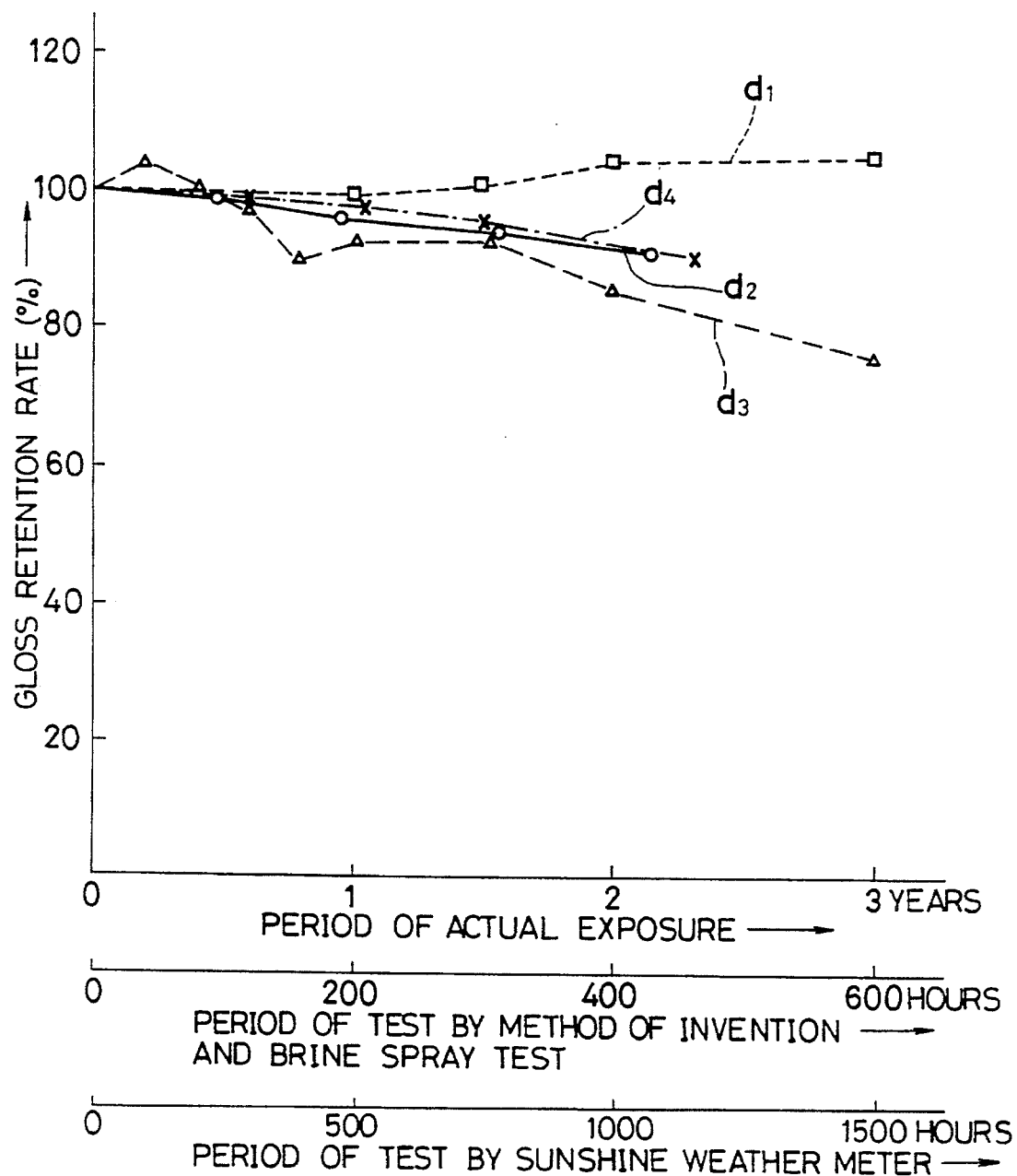
Figure 12:
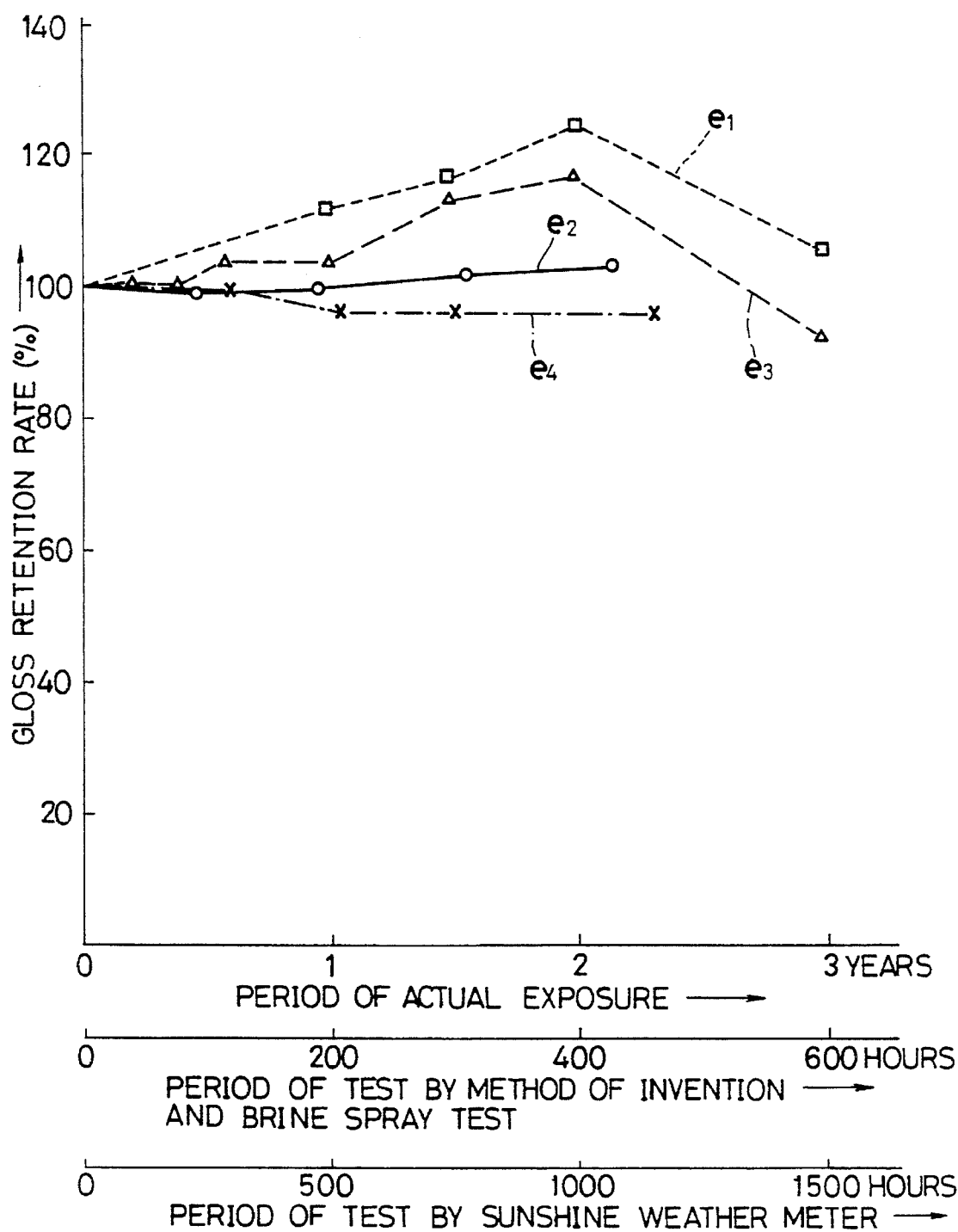

FIGS. 10, 11 and 12 show the changes in the gloss retention rate as observed with samples of Al—Zn-plated steel sheet coated with vinyl chloride sol, galvanized steel sheet coated with fluororesin and the fluororesin laminate galvanized steel sheet, respectively, when these samples were tested by the actual exposure, testing method of the invention and the conventional testing methods 1 and 2, respectively. In the case of the actual exposure test, all the samples showed small values of changes in the gloss retention rate as shown by the curves $c_1$, $d_1$ and $e_1$. The results of the test by the testing method of the invention also showed small changes in the gloss retention rate as shown by curves $c_2$, $d_2$ and $e_2$, thus proving high degree of closeness of correlation to the actual exposure test. In contrast, the results of the test conducted in accordance with the conventional testing method 1 showed a large reduction in the gloss retention rate particularly in the case of the sample of the Al—Zn-plated steel sheet with vinyl chloride sol, as will be seen from the curve $c_3$, thus exhibiting a significant difference from the results of the actual exposure test.

FIG. 13 shows the changes in the gloss retention rates exhibited by the samples of the galvanized steel sheets coated with polyester as observed when these samples were tested by the actual exposure, the testing method of the invention and the conventional testing methods 1 and 2. As shown by the curve $f_1$, the sample tested by the actual exposure showed a rapid reduction in the gloss retention rate in the period of 24 months after the commencement of the test and thereafter no significant change was observed. The sample tested by the testing method of the present invention showed a similar tendency: namely, a rapid reduction in the gloss retention rate was observed when 200 hours has elapsed after the start of the test, as shown by the curve $f_2$. The conventional testing method 1 also showed a drastic decrease in the gloss retention rate after elapse of 200 hours from the start of the test, as shown by the curve $f_3$. This, however, seems to be attributable to the presence of light rays of wavelengths of 300 nm or less in the lights from the light source.

As stated before, each of the same samples (a) to (f) used in the tests described hereinbefore was tested by the same testing methods after forming scratches reaching the underlying metallic layer, and the state of corrosion in the scratched portion was observed to obtain the result as shown in Table 1. The sample used in the actual exposure test, however, had no scratch, and the state of corrosion was observed at a cut sectional surface of the sample and compared with the results of other testing methods on a assumption that the corrosion state at the cut cross-section is substantially the same as that shown by scratched portions of the samples.

TABLE 1

| Samples | Method of Invention | Actual Exposure | Conventional Method 1 | Conventional Method 2 |
|---|---|---|---|---|
| a | white rust | white rust red rust | black rust | heavy white rust |
| b | white rust red rust | red rust | slight white rust | heavy white rust |
| c | red rust | white rust red rust | no rust | slight black rust |
| d | white rut | white rust red rust | white rust | slight white rust |
| e | slight white rust | white rust red rust | slight white rust | slight white rust |
| f | white rust red rust | white rust red rust | slight white rust | white rust red rust |

The states of corrosion shown in Table 1 are those obtained 432 hours after the start of the test in case of the method of the invention, 30 months after the start of the test in case of the actual exposure test, 1500 hours after the start of the test in case of the conventional method 1 and 450 hours after the start of the test in case of the conventional method 2, respectively.

Table 2 shows the states of the coating layers around the scratched portions of the samples (cut surface in case of actual exposure test) as observed after expiration of the same testing periods as those explained in connection with the test results shown in Table 1.

TABLE 2

| Samples | Method of Invention | Actual Exposure | Conventional Method 1 | Conventional Method 2 |
|---|---|---|---|---|
| a | end swell | no change | slight end swell | no change |
| b | end swell | no change | no change | no change |
| c | no change | no change | end swell | no change |
| d | end swell | end swell | slight end swell | no change |
| e | end swell | end swell | no change | no change |
| f | end swell | end swell | end swell | no change |

As will be seen from Table 1, the weather resistance testing method of the present invention can realize, in quite a short time of about 400 hours, a state of corrosion equivalent to that obtained in 30 months of actual exposure. Thus, the method of the invention can promote the degradation also in the aspect of corrosion.

Referring now to Table 2, the weather resistance testing method of the present invention can develop a degradation which is equivalent to or heavier than that obtained in 30 months of the actual exposure, thus proving the possibility of promoting the degradation also in the aspect of the state of the coating layer.

As will be understood from the results of tests described hereinbefore, the weather resistance testing method of the present invention can realize, in quite a short time, a degradation of a degree which very closely approximates that of the degradation caused by a long period of actual exposure, thus proving high degree of correlation between the test results and the natural degradation.

The embodiment described hereinbefore incorporated, as the light source unit, a combination of a metal halide lamp of wavelength ranging between 250 and 550 nm and a filter for restricting the wavelength substantially to a range of 300 to 450 nm, the light source unit illuminating the sample surface at an ultraviolet intensity of 80±5 mW/cm$^2$. This, however, is only illustrative and the invention can be carried out with different types of light source unit such as an artificial light source including ultraviolet rays of an intensity not lower than several tens of mW/cm$^2$ together with visible or infrared rays. The advantages of the invention described before can be obtained even when such an alternative light source is used.

What is claimed is:

1. An apparatus for performing a weather resistance test on a composite material having a metallic, inorganic or an organic base member and an organic material covering the base member, comprising:

sample holding means disposed in a sample chamber for holding a sample of said composite material;

irradiating means including an artificial light source for irradiating light substantially in the ultraviolet light area to one surface of said sample;

dipping means for holding the sample in a horizontal position and applying a corrosive ionized aqueous solution selected from the group consisting, of salt, acid and alkali in a liquid state to said sample causing the aqueous solution to stagnate for a predetermined period of time;

dew condensation means including temperature control means disposed in said sample holding means and moistening means disposed in said sample chamber for causing dew condensation on said surface of said sample;

cleaning means for cleaning said surface of said sample;

steaming means including heating means disposed in said sample chamber and said moistening means for steaming said sample in an atmosphere of high temperature and high humidity; and control means for controlling execution of operations of said irradiating means, said dipping means, said dew condensation means, said cleaning means and said steaming means in a predetermined manner, wherein said control means is adapted to sequentially execute a first step in which the operation of said cleaning means is conducted after the operation of said irradiating means and the operation of said dipping means is conducted after the operation of said cleaning means, a second step in which a second operation of said dipping means is conducted after the operation of said dew condensation means, and a third step in which the operation of said irradiating means is conducted after the operation of said steaming means.

2. An apparatus according to claim 1, wherein said sample holding means includes a sample holder tray which is pivotally supported at its one end for a pivoting movement between an inclined position for enabling operation of said cleaning means and a horizontal position for enabling operation of said dipping means.

* * * * *